(12) United States Patent
Spratt et al.

(10) Patent No.: US 9,498,254 B2
(45) Date of Patent: Nov. 22, 2016

(54) BOTTOM-LOADING BONE ANCHOR ASSEMBLIES

(71) Applicant: MEDOS INTERNATIONAL SARL, Le Locle (CH)

(72) Inventors: Frank Spratt, Middleboro, MA (US); Ralf Klabunde, Winterthur (CH); Thibault Chandanson, Villers le Lac (FR); Richard W. Fournier, New Bedford, MA (US)

(73) Assignee: Medos International Sarl, Le Locle (CH)

( * ) Notice: Subject to any disclaimer, the term of this patent is extended or adjusted under 35 U.S.C. 154(b) by 0 days.

(21) Appl. No.: 14/735,326

(22) Filed: Jun. 10, 2015

(65) Prior Publication Data

US 2015/0272626 A1 Oct. 1, 2015

Related U.S. Application Data

(62) Division of application No. 13/829,000, filed on Mar. 14, 2013, now abandoned.

(51) Int. Cl.
*A61B 17/70* (2006.01)

(52) U.S. Cl.
CPC ....... *A61B 17/7032* (2013.01); *A61B 17/7037* (2013.01)

(58) Field of Classification Search
USPC .......................................... 606/268–269, 266
See application file for complete search history.

(56) References Cited

U.S. PATENT DOCUMENTS

| 5,879,350 A | 3/1999 | Sherman et al. |
| 6,053,917 A | 4/2000 | Sherman et al. |
| 6,056,753 A | 5/2000 | Jackson |
| 6,113,601 A | 9/2000 | Tatar |

(Continued)

FOREIGN PATENT DOCUMENTS

| EP | 1 570 794 A1 | 9/2005 |
| EP | 2 272 451 A1 | 1/2011 |

(Continued)

OTHER PUBLICATIONS

Inter Partes Review: http://openjurist.org/127/f3d/1048/in-re-charles-p-morris, In re Morris, accessed Feb. 21, 2015.

(Continued)

*Primary Examiner* — Jan Christopher Merene
(74) *Attorney, Agent, or Firm* — Nutter McClennen & Fish LLP

(57) ABSTRACT

Bone anchor assemblies are disclosed herein and include bone anchors, receiver members, and closure mechanisms. In one embodiment, a receiver member can be configured to seat a portion of a bone anchor and to receive a spinal fixation element, such as a rod. In an exemplary embodiment, the receiver member is bottom-loading and can include a seat having an opening that can be selectively increased and decreased in size so as to allow a bone anchor to be bottom-loaded. A force can be applied to the receiver member to increase a size of the opening, allowing a portion of the anchor to pass through the opening and into the seat. A closure element can be coupled to the receiver member and can apply a force to decrease a size of the seat and a size of the opening, angularly fixing the receiver member relative to the bone anchor.

14 Claims, 22 Drawing Sheets

(56) References Cited

U.S. PATENT DOCUMENTS

| | | | |
|---|---|---|---|
| 6,224,598 B1* | 5/2001 | Jackson | A61B 17/7032 606/264 |
| 6,280,442 B1 | 8/2001 | Barker et al. | |
| 6,660,004 B2 | 12/2003 | Barker et al. | |
| 6,736,820 B2 | 5/2004 | Biedermann et al. | |
| 6,918,911 B2 | 7/2005 | Biedermann et al. | |
| 6,974,460 B2 | 12/2005 | Carbone et al. | |
| 7,022,122 B2 | 4/2006 | Amrein et al. | |
| 7,087,057 B2 | 8/2006 | Konieczynski et al. | |
| 7,090,674 B2 | 8/2006 | Doubler et al. | |
| 7,179,261 B2 | 2/2007 | Sicvol et al. | |
| 7,186,255 B2 | 3/2007 | Baynham et al. | |
| 7,322,981 B2 | 1/2008 | Jackson | |
| 7,325,470 B2 | 2/2008 | Kay et al. | |
| 7,445,627 B2 | 11/2008 | Hawkes et al. | |
| 7,530,992 B2 | 5/2009 | Biedermann et al. | |
| 7,615,068 B2 | 11/2009 | Timm et al. | |
| 7,686,833 B1 | 3/2010 | Muhanna et al. | |
| 7,727,261 B2 | 6/2010 | Barker et al. | |
| 7,766,946 B2 | 8/2010 | Bailly | |
| 7,785,354 B2 | 8/2010 | Biedermann et al. | |
| 7,789,900 B2 | 9/2010 | Levy et al. | |
| 8,007,522 B2 | 8/2011 | Hutchinson | |
| 8,092,494 B2 | 1/2012 | Butler et al. | |
| 8,100,946 B2 | 1/2012 | Strausbaugh et al. | |
| 8,162,989 B2 | 4/2012 | Khalili | |
| 8,167,910 B2 | 5/2012 | Nilsson | |
| 8,167,912 B2 | 5/2012 | Jacofsky et al. | |
| 8,197,517 B1 | 6/2012 | Lab et al. | |
| 8,197,518 B2 | 6/2012 | Hammill, Sr. et al. | |
| 8,211,108 B2 | 7/2012 | Matityahu | |
| 8,221,472 B2 | 7/2012 | Peterson et al. | |
| 8,257,399 B2* | 9/2012 | Biedermann | A61B 17/7032 606/264 |
| 8,273,112 B2 | 9/2012 | Garamszegi et al. | |
| 8,287,576 B2 | 10/2012 | Barrus | |
| 8,298,274 B2 | 10/2012 | Barker, Jr. et al. | |
| 8,308,782 B2 | 11/2012 | Jackson | |
| 8,313,515 B2 | 11/2012 | Brennan et al. | |
| 8,313,516 B2 | 11/2012 | Konieczynski et al. | |
| 8,337,527 B2* | 12/2012 | Hawkins | A61B 17/705 606/151 |
| 8,337,530 B2 | 12/2012 | Hestad et al. | |
| 8,409,260 B2 | 4/2013 | Biedermann et al. | |
| 8,672,978 B2 | 3/2014 | Dant et al. | |
| 8,764,805 B2* | 7/2014 | Biedermann | A61B 17/7037 606/269 |
| 2003/0004511 A1 | 1/2003 | Ferree | |
| 2003/0055426 A1 | 3/2003 | Carbone et al. | |
| 2003/0100904 A1* | 5/2003 | Biedermann | A61B 17/7032 606/272 |
| 2005/0096653 A1 | 5/2005 | Doubler et al. | |
| 2005/0154391 A1 | 7/2005 | Doherty et al. | |
| 2005/0251141 A1* | 11/2005 | Frigg | A61B 17/7041 606/301 |
| 2005/0267472 A1* | 12/2005 | Biedermann | A61B 17/7037 606/308 |
| 2006/0149235 A1* | 7/2006 | Jackson | A61B 17/7032 606/328 |
| 2006/0149265 A1 | 7/2006 | James et al. | |
| 2007/0173825 A1* | 7/2007 | Sharifi-Mehr | A61B 17/705 606/272 |
| 2008/0051780 A1* | 2/2008 | Vaidya | A61B 17/7035 606/86 A |
| 2008/0119852 A1 | 5/2008 | Dalton et al. | |
| 2008/0154308 A1 | 6/2008 | Sherman et al. | |
| 2008/0200956 A1 | 8/2008 | Beckwith et al. | |
| 2008/0243193 A1* | 10/2008 | Ensign | A61B 17/7032 606/305 |
| 2008/0269809 A1 | 10/2008 | Garamszegi | |
| 2008/0312655 A1* | 12/2008 | Kirschman | A61B 17/7032 606/308 |
| 2009/0005813 A1 | 1/2009 | Crall et al. | |
| 2009/0018591 A1 | 1/2009 | Hawkes et al. | |
| 2009/0198280 A1* | 8/2009 | Spratt | A61B 17/7038 606/267 |
| 2009/0287261 A1 | 11/2009 | Jackson | |
| 2010/0114167 A1* | 5/2010 | Wilcox | A61B 17/7004 606/250 |
| 2010/0114174 A1 | 5/2010 | Jones et al. | |
| 2010/0198270 A1 | 8/2010 | Barker et al. | |
| 2010/0198272 A1 | 8/2010 | Keyer et al. | |
| 2011/0245876 A1 | 10/2011 | Brumfield | |
| 2011/0282399 A1 | 11/2011 | Jackson | |
| 2011/0288599 A1 | 11/2011 | Michielli et al. | |
| 2011/0295321 A1 | 12/2011 | Hutchinson | |
| 2012/0010661 A1 | 1/2012 | Farris et al. | |
| 2012/0035670 A1 | 2/2012 | Jackson et al. | |
| 2012/0089194 A1 | 4/2012 | Strausbaugh et al. | |
| 2012/0197313 A1 | 8/2012 | Cowan | |
| 2012/0253404 A1 | 10/2012 | Timm et al. | |
| 2012/0303070 A1 | 11/2012 | Jackson | |
| 2012/0310290 A1 | 12/2012 | Jackson | |
| 2012/0316605 A1 | 12/2012 | Palagi | |
| 2012/0330364 A1 | 12/2012 | Jacofsky et al. | |
| 2013/0053901 A1 | 2/2013 | Cormier et al. | |
| 2013/0096618 A1 | 4/2013 | Chandanson et al. | |
| 2014/0277159 A1 | 9/2014 | Spratt et al. | |
| 2015/0080960 A1* | 3/2015 | Biedermann | A61B 17/7037 606/278 |

FOREIGN PATENT DOCUMENTS

| | | |
|---|---|---|
| WO | 2008/024937 A2 | 2/2008 |
| WO | 2011/127065 A1 | 10/2011 |
| WO | 2012/024665 A2 | 2/2012 |
| WO | 2013/028851 A1 | 2/2013 |

OTHER PUBLICATIONS

[No Author Listed] A New Angle on Correction. Expedium. DePuy. 2009. 2 pages.

[No Author Listed] Straight Talk with Expedium. Expedium. 10 pages. Jul. 2007.

[No Author Listed] Surgical Technique Guide and Ordering Information. Expedium. DePuy Spine Inc. Sep. 2011. 24 Pages.

[No Author Listed] Value Analysis Brief—Expedium Favored Angle Screw. DePuy Synthes Spine. Aug. 2012. 4 pages.

[No Author Listed] Viper 2 MIS Spine System. System Guide. DePuy Spine Inc. Sep. 2011. 60 pages.

U.S. Appl. No. 13/804,012, filed Mar. 14, 2013, Bone Anchors and Surgical Instruments With Integrated Guide Tips.

U.S. Appl. No. 13/826,161, filed Mar. 14, 2013, Bone Anchor Assemblies and Methods With Improved Locking.

U.S. Appl. No. 13/827,092, filed Mar. 14, 2013, Locking Compression Members for Use With Bone Anchor Assemblies and Methods.

U.S. Appl. No. 13/828,236, filed Mar. 14, 2013, Bone Anchor Assemblies With Multiple Component Bottom Loading Bone Anchors.

U.S. Appl. No. 13/828,882, filed Mar. 14, 2013, Bottom-Loading Bone Anchor Assemblies and Methods.

U.S. Appl. No. 13/829,000, filed Mar. 14, 2013, Bottom-Loading Bone Anchor Assemblies.

U.S. Appl. No. 61/706,860, filed Sep. 28, 2012, Devices and Methods for Breaking and Retaining Surgical Reduction Tabs.

U.S. Appl. No. 61/707,062, filed Sep. 28, 2012, Bone Anchor Assemblies.

\* cited by examiner

BOTTOM-LOADING BONE ANCHOR ASSEMBLIES

CROSS-REFERENCE TO RELATED APPLICATIONS

This application is a divisional of U.S. patent application Ser. No. 13/829,000, filed Mar. 14, 2013, entitled "Bottom-Loading Bone Anchor Assemblies," now abandoned, which application is hereby incorporated by reference in its entirety as though fully set forth herein.

FIELD

The present invention relates to methods and devices for correcting a spine, and more specifically to bone anchor assemblies and methods of using the same.

BACKGROUND

Spinal fixation devices are used in orthopedic surgery to align and/or fix a desired relationship between adjacent vertebral bodies. Such devices typically include a spinal fixation element, such as a relatively rigid fixation rod, that is coupled to adjacent vertebrae by attaching the element to various anchoring devices, such as hooks, bolts, wires, or screws. The fixation rods can have a predetermined contour that has been designed according to the properties of the target implantation site, and once installed, the instrument holds the vertebrae in a desired spatial relationship, either until desired healing or spinal fusion has taken place, or for some longer period of time.

Spinal fixation devices can be anchored to specific portions of the vertebra. Since each vertebra varies in shape and size, a variety of anchoring devices have been developed to facilitate engagement of a particular portion of the bone. Pedicle screw assemblies, for example, have a shape and size that is configured to engage pedicle bone. Such screws typically include a bone anchor with a threaded shank that is adapted to be threaded into a vertebra, and a rod-receiving element, usually in the form of a head having opposed U-shaped slots formed therein. The shank and rod-receiving assembly can be provided as a monoaxial assembly, whereby the rod-receiving element is fixed with respect to the shank, a unidirectional or uniplanar assembly, wherein the shank is limited to movement in a particular direction, e.g., within a single plane, or a polyaxial assembly, whereby the rod-receiving element has free angular movement with respect to the shank. In use, the shank portion of each screw is threaded into a vertebra, and once properly positioned, a fixation rod is seated into the rod-receiving element of each screw. The rod is then locked in place by tightening a set-screw, plug, or similar type of fastening mechanism onto the rod-receiving element.

In certain procedures, it is desirable to utilize a bone screw having a large diameter shank. Such large diameter bone screws often utilize a bottom-loading configuration, in which the head of the threaded shank is loaded into an opening in the bottom of the rod-receiving element. This can be done during manufacturing, or intraoperatively either before or after the threaded shank is implanted in bone. This allows the diameter of the shank to remain independent of the size of the opening formed in the rod-receiving element. However, the ability to perform correctional techniques with such bottom-loading bone anchor assemblies can be limited. These devices must be able to withstand correctional forces applied thereto when the rod-receiving element is angulated relative to the shank and/or during bending of a spinal fixation rod seated therein.

Accordingly, there remains a need for improved devices and methods for correcting a spine, and in particular to improved bottom-loading anchor assemblies and methods.

SUMMARY OF THE INVENTION

Bone anchor assemblies and methods of using the same are provided herein. In one embodiment, a bone anchor assembly is provided having a bone anchor and a receiver member. The bone anchor can have a proximal head and a distal threaded portion. The receiver member can have a proximal portion with opposed arms configured to receive a spinal fixation rod therebetween. A distal portion of the receiver member can have a polyaxial seat formed therein and configured to polyaxially seat the proximal head of the bone anchor. In one embodiment, the opposed arms of the receiver member can be configured to move toward one another to cause a size of the polyaxial seat to increase, and the opposed arms can be configured to move away from one another to cause the size of the polyaxial seat to decrease.

The polyaxial seat in the receiver member can vary in a number of ways. In certain aspects, an outer diameter of the proximal head of the bone anchor can be greater than a size of an opening formed in a distal end of the receiver member and extending into the polyaxial seat. The polyaxial seat can be configured to frictionally engage the proximal head of the bone anchor when the head is seated therein and no closure mechanism is applied to the receiver member.

The receiver member can have various features. For example, at least one relief slot can be formed in the distal portion of the receiver member and it can be configured to allow the opposed arms to move toward and away from one another and to allow the size of the polyaxial seat to increase and decrease. In certain aspects, the distal portion of the receiver member can include opposed relief slots formed therein and extending proximally from a distal-most end thereof. In one embodiment, the at least one relief slot can be substantially T-shaped. In another embodiment, the opposed arms of the receiver member can define a U-shaped recess configured to seat a spinal fixation rod, the U-shaped recess can include opposed flat surfaces thereon for seating spinal fixation rods of differing diameters. The opposed flat surfaces can extend at an oblique angle relative to a longitudinal axis of the receiver member. In yet another embodiment, the receiver member can include opposed flat surfaces formed therein and configured to limit movement of the distal threaded portion of the bone anchor along a single plane of motion.

The bone anchor assembly can further include a closure mechanism configured to mate to the opposed arms and to cause the opposed arms to move away from one another. This can cause the distal portion of the receiver member to compress around the proximal head of the bone anchor to prevent removal of the proximal head from the polyaxial seat in the receiver member. In certain aspects, the closure mechanism is a threaded set screw having an outer diameter that increases in a distal-to-proximal direction.

Methods for implanting a bone anchor are also provided. This can include implanting a threaded shank of a bone anchor in bone and positioning a spinal fixation rod within a u-shaped recess in a receiver member movably coupled to a proximal head formed on the threaded shank of the bone anchor. The method can further include applying a closure mechanism to the receiver member to cause a distal portion of the receiver member to compress around the proximal head of the bone anchor and thereby lock the receiver member in a fixed position relative to the bone anchor.

The method can vary in a number of ways. For example, the closure mechanism can include an outer set screw that is threaded into a proximal portion of the receiver member, and the method can further include threading an inner set screw into the outer set screw to lock the spinal fixation rod within the receiver member. In certain aspects, the closure mechanism can be tapered such that the closure mechanism causes opposed proximal arms of the receiver member to move away from one another thereby causing the distal portion of the receiver member to compress around the proximal head of the bone anchor. In another embodiment, the receiver member can be limited to movement within a single plane of motion relative to the bone anchor.

The present invention further provides devices, systems, and methods as claimed.

BRIEF DESCRIPTION OF THE DRAWINGS

The invention will be more fully understood from the following detailed description taken in conjunction with the accompanying drawings, in which.

DETAILED DESCRIPTION

Figure 1A:
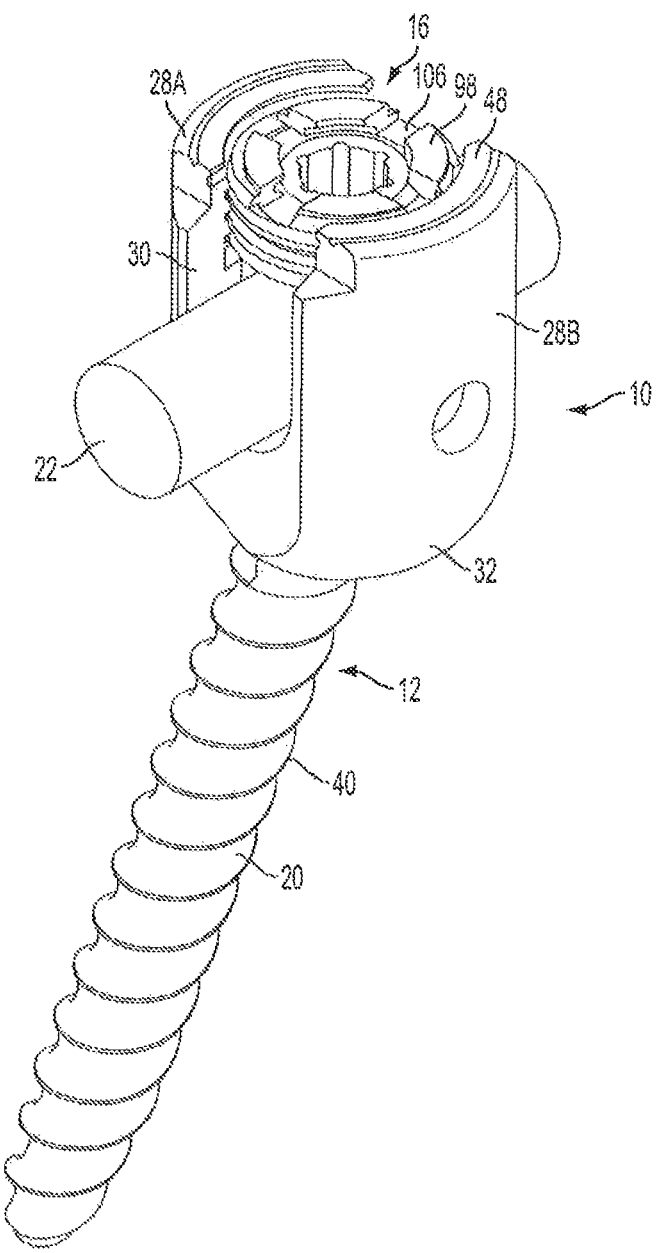
FIG. 1A is a perspective view of a prior art bone anchor assembly.
Figure 1B:
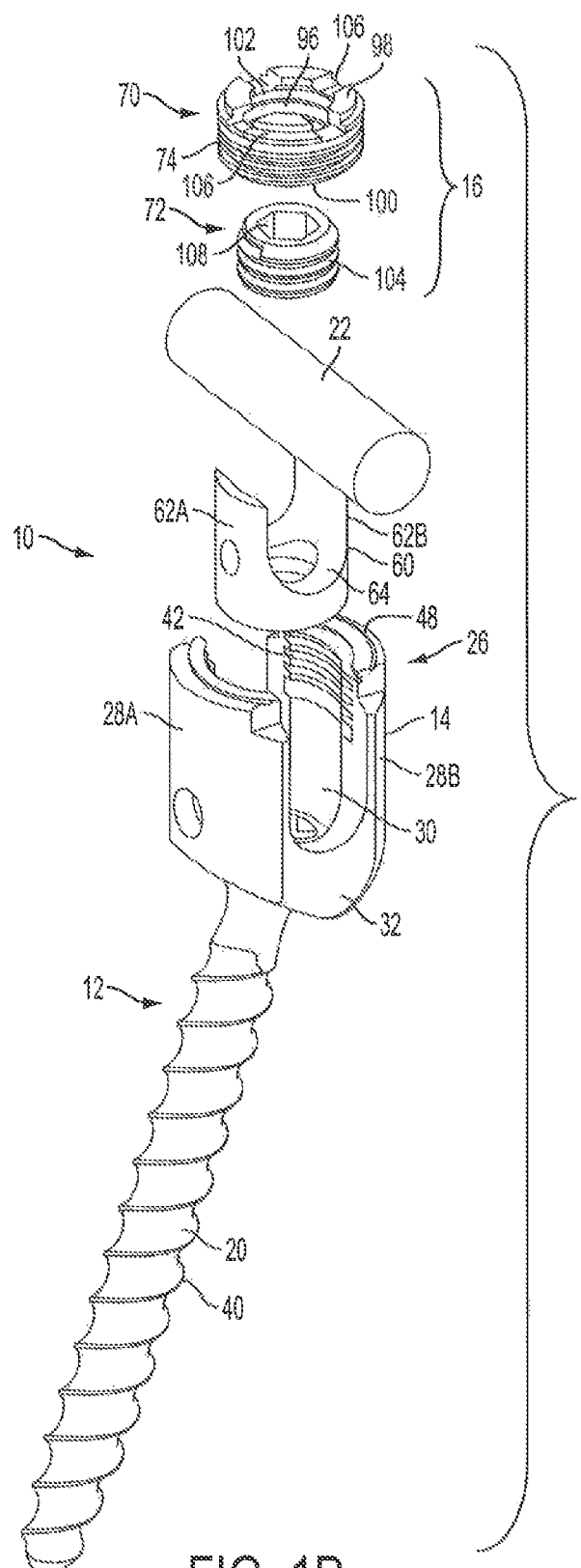
FIG. 1B is an exploded view of the bone anchor assembly of FIG. 1A.
Figure 1C:
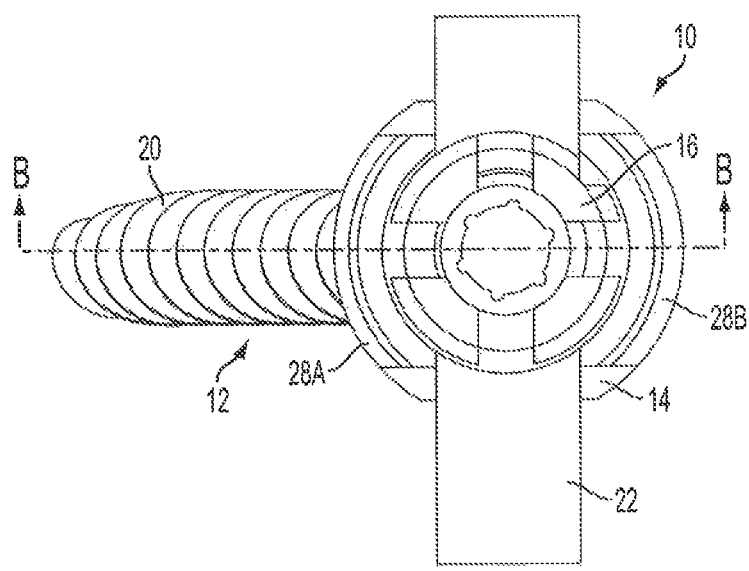
FIG. 1C is a top view of the bone anchor assembly of FIG. 1A.
Figure 1D:
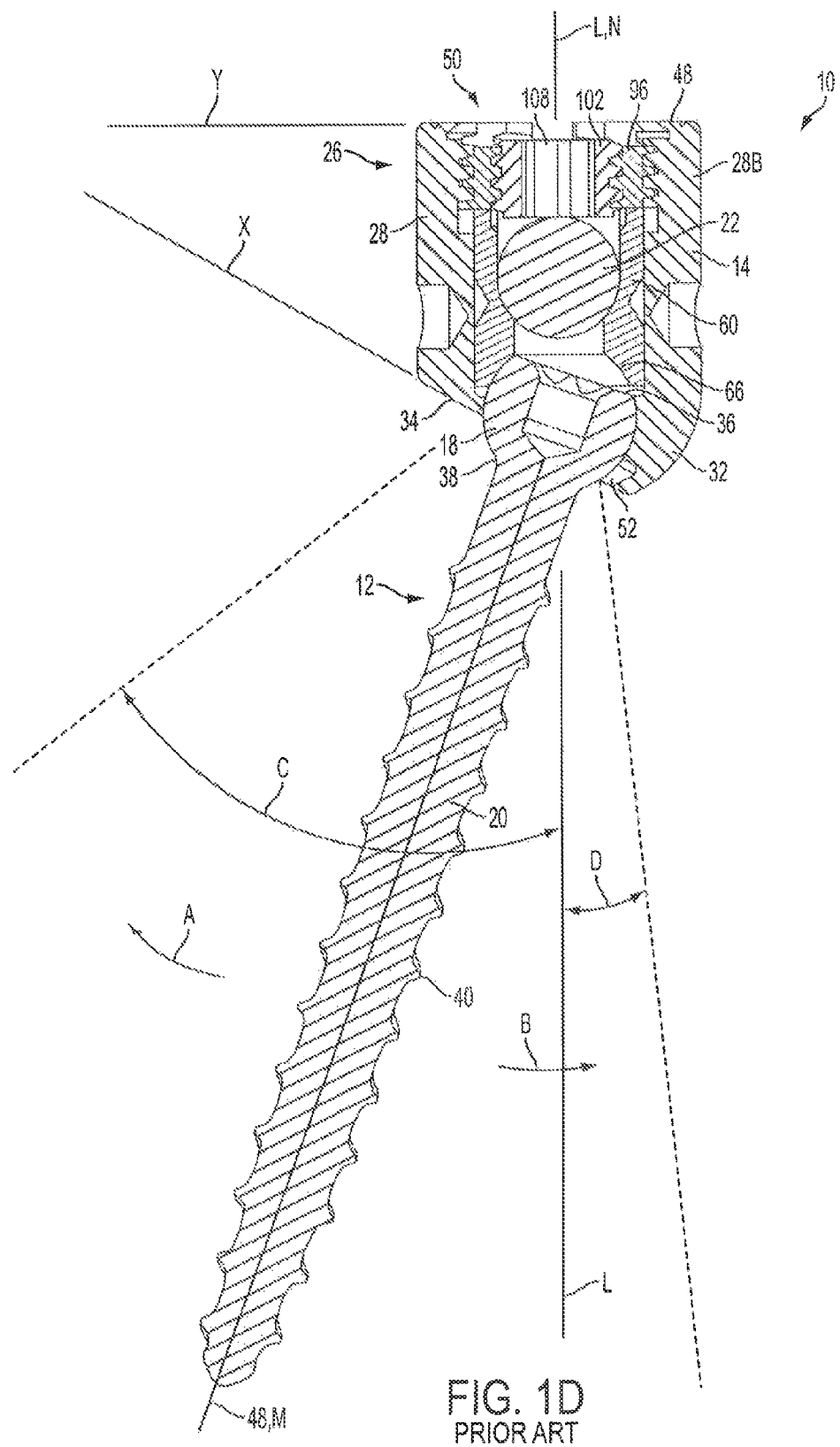
FIG. 1D is a cross-sectional view of the bone anchor assembly of FIG. 1A.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention Further, in the present disclosure, like-numbered components of the embodiments generally have similar features, and thus within a particular embodiment each feature of each like-numbered component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

The bone anchor assemblies disclosed herein can include any number of features shown in the prior art and any combination of features shown in the different embodiments of the receiver members, bone anchors, and closure elements.

Various bone anchor assemblies are disclosed herein and include bone anchors, receiver members, and closure mechanisms. In general, a receiver member can be configured to seat or frictionally engage a portion of a bone anchor therein and can be configured to receive a spinal fixation element, such as a spinal rod. In an exemplary embodiment, the receiver member is bottom-loading and can include a seat having an opening that can be selectively increased and decreased in size so as to allow a bone anchor to be bottom-loaded into the receiver member and seated within a polyaxial seat formed within the receiver member. A force can be applied to the receiver member to increase a size of the opening in the receiver member, allowing a portion of the bone anchor to pass through the opening and into the seat. A closure element can be coupled to the receiver element and can apply a force to decrease a size of the seat and a size of the opening in the receiver member, angularly fixing the receiver member relative to the bone anchor. The bone anchor assemblies disclosed herein can be used during open and minimally invasive surgical procedures.

FIGS. 1A-1D illustrate a prior art bone anchor assembly 10 including a bone anchor 12, a receiver member 14 for receiving a spinal fixation element, such as a spinal rod 22, to be coupled to the bone anchor 12, and a closure mechanism 16 to capture or lock a spinal fixation element within the receiver member 14 and fix the spinal fixation element with respect to the receiver member 14. The bone anchor 12 includes a proximal head 18 and a distal shaft 20 configured to engage bone. The receiver member 14 has a proximal end 26 having a pair of spaced apart arms 28A, 28B defining a recess 30 therebetween and a distal end 32 having a distal end surface 34 defining an opening through which at least a portion of the bone anchor 12 extends. The closure mechanism 16 can be positionable between and can engage the arms 28A, 28B to capture or lock a spinal fixation element, e.g., a spinal rod 22, within the receiver member 14 and fix the spinal fixation element with respect to the receiver member 14.

The proximal head 18 of the bone anchor 12 is generally in the shape of a truncated sphere having a planar proximal surface 36 and an approximately spherically-shaped distal surface 38. The proximal head 18 of the bone anchor 12 can also have a bore or recess extending along a longitudinal axis of the proximal head 18 that can receive and mate with a driver tool. The illustrated bone anchor assembly is a polyaxial bone anchor designed for posterior implantation in the pedicle or lateral mass of a vertebra. The proximal head 18 of the bone anchor 12 engages the distal end 32 of the receiver member 14 in a ball and socket like arrangement in which the proximal head 18 the distal shaft 20 can pivot relative to the receiver member 14. The distal surface 38 of the proximal head 18 of the bone anchor 12 and a mating surface within the distal end 32 of the receiver member 14 can have any shape that facilitates this arrangement, including, for example, spherical (as illustrated), toroidal, conical, frustoconical, and any combinations of these shapes.

The distal shaft 20 of the bone anchor 12 can be configured to engage bone and, in the illustrated embodiment, includes an external bone engaging thread 40. The thread form for the distal shaft 20, including the number of threads, the pitch, the major and minor diameters, and the thread shape, can be selected to facilitate connection with bone. Exemplary thread forms are disclosed in U.S. Patent Application Publication No. 2011/0288599, filed on May 18, 2011, and in U.S. Provisional Patent Application Ser. No. 61/527,389, filed Aug. 25, 2011, both of which are incorporated herein by reference. The distal shaft 20 can also include other structures for engaging bone, including a hook. The distal shaft 20 of the bone anchor 12 can be cannulated, having a central passage or cannula extending the length of the bone anchor to facilitate delivery of the bone anchor over a guide wire in, for example, minimally-invasive procedures. Other components of the bone anchor assembly, including, for example, the closure member 16, the receiver member 14, and the compression member 60 (discussed below) can be cannulated or otherwise have an opening to permit delivery over a guide wire. The distal shaft 20 can also include one or more sidewall openings or fenestrations that communicate with the cannula to permit bone in-growth or to permit the dispensing of bone cement or other materials through the bone anchor 12. The sidewall openings can extend radially from the cannula through the sidewall of the distal shaft 20. Exemplary systems for delivering bone cement to the bone anchor assembly 10 and alternative bone anchor configurations for facilitating cement delivery are described in U.S. Patent Application Publication No. 2010/0114174, filed on Oct. 29, 2009, which is hereby incorporated herein by reference. The distal shaft 20 of the bone anchor 12 can also be coated with materials to permit bone growth, such as, for example, hydroxyl apatite, and the bone anchor assembly 10 can be coated partially or entirely with anti-infective materials, such as, for example, tryclosan.

The proximal end 26 of the receiver member 14 includes a pair of spaced apart arms 28A, 28B defining a U-shaped recess 30 therebetween for receiving a spinal fixation element, e.g., a spinal rod 22. Each of the arms 28A, 28B can extend from the distal end 32 of the receiver member 14 to a free end. The outer surfaces of each of the arms 28A, 28B can include a feature, such as a recess, dimple, notch, projection, or the like, to facilitate connection of the receiver member 14 to instruments. For example, the outer surface of each arm 28A, 28B can include an arcuate groove at the respective free end of the arms. Such grooves are described in more detail in U.S. Pat. No. 7,179,261, issued on Feb. 20, 2007, which is hereby incorporated herein by reference. At least a portion of the proximal end surface 48 of the receiver member 12 defines a plane Y. The receiver member 14 has a central longitudinal axis L.

The distal end 32 of the receiver member 14 includes a distal end surface 34 which is generally annular in shape defining a circular opening through which at least a portion of the bone anchor 12 extends. For example, the distal shaft 20 of the bone anchor 12 can extend through the opening. At least a portion of the distal end surface 34 defines a plane X.

The bone anchor 12 can be selectively fixed relative to the receiver member 14. Prior to fixation, the bone anchor 12 is movable relative to the receiver member 14 within a cone of angulation generally defined by the geometry of the distal end 32 of the receiver member and the proximal head 18 of the bone anchor 12. The illustrated bone anchor is a favored-angle polyaxial screw in which the cone of angulation is biased in one direction. In this manner, the bone anchor 12 is movable relative to the receiver member 14 in at least a first direction, indicated by arrow A in FIG. 1D, at a first angle C relative to the central longitudinal axis L of the receiver member 14. The bone anchor 12 is also movable in at least a second direction, indicated by arrow B in FIG. 1D, at a second angle D relative to the longitudinal axis L. The first angle C is greater than the second angle D and, thus, the shaft 20 of the bone anchor 12 is movable more in the direction indicated by arrow A than in the direction indicated by arrow B. The distal shaft 20 of the bone anchor 12 defines a neutral axis 48 with respect to the receiver member 14. The neutral axis 48 can be perpendicular to the plane X defined by the distal end surface 34 and intersects the center point of the opening in the distal end surface 34 through which the distal shaft 20 of the bone anchor 12 extends. The neutral axis 48 can be oriented at an angle to the central longitudinal axis L of the receiver member 14. The plane Y defined by at least a portion of the proximal end surface 48 of the receiver member 14 intersects the plane X defined by at least a portion of the distal end surface 34 of the receiver member 12. The proximal end 26 of the receiver member 14 can include a proximal first bore 50 coaxial with a first central longitudinal axis N (which is coincident with longitudinal axis L) and a distal second bore 52 coaxial with a second central longitudinal axis M (which is coincident with the neutral axis 48) and the first central longitudinal axis N and second central longitudinal axis M can intersect one another. The angle between the plane X and the plane Y and the angle between the axis L and the axis M can be selected to provide the desired degree of biased angulation. Examples of favored angled polyaxial screws are described in more detail in U.S. Pat. No. 6,974,460, issued on Dec. 13, 2005, and in U.S. Pat. No. 6,736,820, issued on May 18, 2004, both of which are hereby incorporated herein by reference. Alternatively, the bone anchor assembly can be a conventional (non-biased) polyaxial screw in which the bone anchor pivots in the same amount in every direction and has a neutral axis that is coincident with the central longitudinal axis L of the receiver member.

The spinal fixation element, e.g., the spinal rod 22, can contact an intermediate element, e.g., a compression member 60 disposed in a receiver member. The compression member 60 can be positioned within the receiver member 14 and interposed between the spinal rod 22 and the proximal head 18 of the bone anchor 12 to compress the distal outer surface 38 of the proximal head 18 into direct, fixed engagement with the distal inner surface of the receiver member 14. The compression member 60 can include a pair of spaced apart arms 62A and 62B defining a U-shaped seat 64 for receiving the spinal rod 22 and a distal surface 66 for engaging the proximal head 18 of the bone anchor 12.

The proximal end 26 of the receiver member 14 can be configured to receive a closure mechanism 16 positionable between and engaging the arms 28A, 28B of the receiver member 14. The closure mechanism 16 can be configured to capture or lock a spinal fixation element, e.g., a spinal rod 22, within the receiver member 14, to fix the spinal rod 22 relative to the receiver member 14, and to fix the bone anchor 12 relative to the receiver member 14. The closure mechanism 16 can be a single set screw having an outer thread for engaging an inner thread 42 provided on the arms 28A, 28B of the receiver member 14. In the illustrated embodiment, however, the closure mechanism 16 comprises an outer set screw 70 positionable between and engaging the arms 28A, 28B of the receiver member 14 and an inner set screw 72 positionable within the outer set screw 70. The outer set screw 70 is operable to act on the compression member 60 to fix the bone anchor 12 relative to the receiver member 14. The inner set screw 72 is operable to act on the spinal rod 22 to fix the spinal rod 22 relative to the receiver member 14. In this manner, the closure mechanism 16 permits the bone anchor 12 to be fixed relative to the receiver member 14 independently of the spinal rod 22 being fixed to the receiver member 14. In particular, the outer set screw 70 can engage the proximal end surfaces of the arms 62A, 62B of the compression member 60 to force the distal surface 66 of the compression member 60 into contact with the proximal head 18 of bone anchor 12, which in turn forces the distal surface 38 of the proximal head 18 into fixed engagement with the distal inner surface of the receiver member 14. The inner set screw 72 can engage the spinal rod 22 to force the spinal rod 22 into fixed engagement with the rod seat 64 of the compression member 60.

The outer set screw 70 includes a first outer thread 74 for engaging a complementary inner thread 42 on the arms 28A, 28B of the receiver member 14. The outer set screw 74 includes a central passage 96 from a top surface 98 of the outer set screw 74 to a bottom surface 100 of the outer set screw 74 for receiving the inner set screw 72. The central passage 96 can includes an inner thread 102 for engaging a complementary outer thread 104 on the inner set screw 72. The thread form for the inner thread 102 and the outer thread 104, including the number of threads, the pitch, major and minor diameter, and thread shape, can be selected to facilitate connection between the components and transfer of the desired axial tightening force. The top surface 98 of the outer set screw 74 can have one or more drive features to facilitate rotation and advancement of the outer set screw 74 relative to the receiver member 14. The illustrated outer set screw 74 includes drive features in the form of a plurality of cut-outs 106 spaced-apart about the perimeter of the top surface 98. The inner set screw 104 can include drive features for receiving an instrument to rotate and advance the inner set screw 72 relative to the outer set screw 74. The illustrated inner set screw 104 includes drive features in the form of a central passage 108 having a plurality of spaced apart, longitudinally oriented cut-outs for engaging complementary features on an instrument.

The bone anchor assembly 10 can be used with a spinal fixation element such as rigid spinal rod 22. The various components of the bone anchor assemblies disclosed herein, as well as the spinal rod 22, can be constructed from various materials, including titanium, titanium alloys, stainless steel, cobalt chrome, PEEK, or other materials suitable for rigid fixation. In other embodiments, the spinal fixation element can be a dynamic stabilization member that allows controlled mobility between the instrumented vertebrae.

Figure 2:
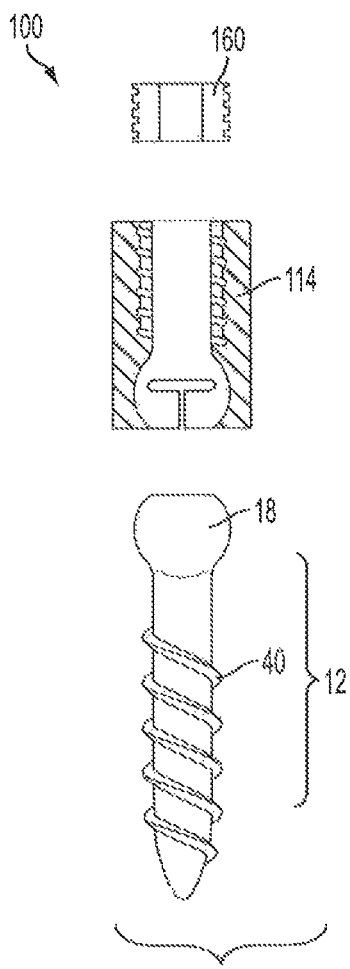
FIG. 2 is an exploded, cross-sectional view of one embodiment of a bone anchor assembly that includes a bone anchor, a receiver member, and a closure mechanism.

FIG. 2 illustrates an exploded view of a bone anchor assembly 100 according to one exemplary embodiment. The bone anchor assembly 100 includes a receiver member 114, a closure mechanism 160, and the bone anchor 12. The bone anchor 12 can have any of the features previously described, including the proximal head 18, the external bone engaging thread 40, and a bore or recess (not shown) for mating with a driver tool. The proximal head 18 of the bone anchor 12 can be polyaxially seated in a distal opening formed in the receiver member 114 such that the receiver member 114 can be pivoted at various angles relative to the bone anchor 114. Unlike the prior art bone anchor assembly 10, the receiver member 114 can be configured to receive a spinal fixation element, e.g., a spinal rod, directly therein and does not require use of a separate compression cap to angularly fix the receiver member 114 relative to the bone anchor 12. Rather, the closure mechanism 160 can be inserted into the receiver member 114 to angularly fix (i.e., lock) the angle of the receiver member 114 relative to the bone anchor, as will be described in greater detail below. A person skilled in the art will appreciate that in other embodiments the receiver member can include a compression cap.

Figure 3A:
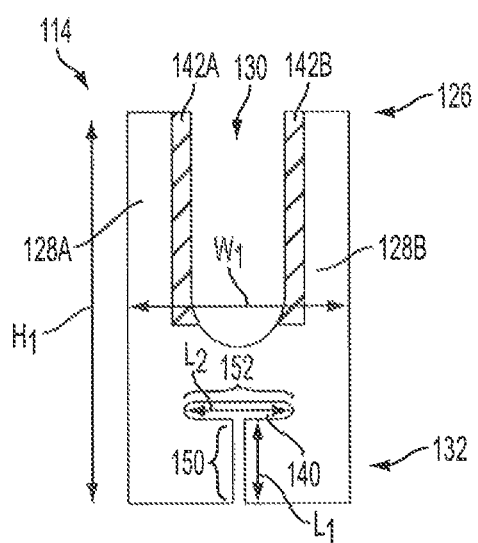
FIG. 3A is a side view of the receiver member of FIG. 2.
Figure 3B:
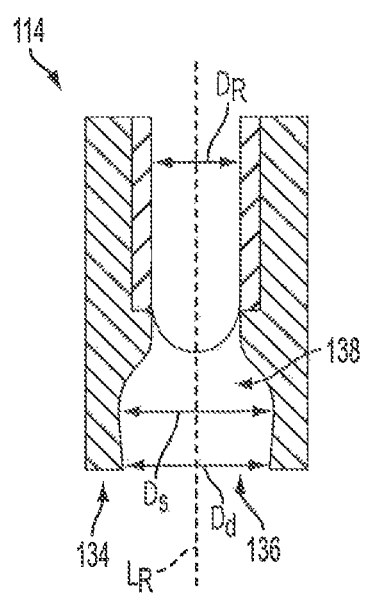
FIG. 3B is a side, cross-sectional view of the receiver member of FIG. 2.

The receiver member 114 can have various sizes, shapes, and configurations, and can include any combination of features described with respect to receiver member 14. As shown in FIG. 3A, a proximal end 126 of the receiver member 114 can include a pair of spaced apart arms 128A, 128B defining a U-shaped recess 130 therebetween for receiving a spinal fixation element. Each of the arms 128A, 128B can extend from a distal end 132 of the receiver member 114 to an open proximal end 126. Outer surfaces of each of the arms 128A, 128B can include a feature (not shown), such as a recess, dimple, notch, projection, or the like, to facilitate connection of the receiver member 114 to instruments. As shown in FIG. 3B, an inner surface of each of the arms 128A, 12B can have one or more surface features, such as threads 142A, 142B formed thereon, the threads 142A, 142B being configured to mate with corresponding threads on a closure mechanism (not shown).

A distal end 132 of the receiver member 114 can have a distal end surface 134 which is generally annular in shape defining a distal opening 136, shown as a circular opening, through which at least a portion of the bone anchor 12 can extend. In the illustrated embodiment, the distal opening 136 can be symmetrical about a longitudinal axis $L_R$ of the receiver member 114, as shown in FIG. 3B. As will be appreciated by a person skilled in the art, the distal opening 136 can be shaped in various ways, including by way of non-limiting example, elliptical, rectangular, pyramidal, etc. While not shown, the distal end surface 134 of the receiver member 114 can be angled, as in the embodiment of FIGS. 1A-1D, such that the receiver member 114 is configured to pivot at different magnitudes in different planes.

As shown in FIG. 3B, a recess or seat 138 can be formed in the distal end 132 of the receiver member 114 and can define the distal opening 136. The seat 138 is generally referred to as a polyaxial seat because, when a portion of the bone anchor 12 is positioned therein, the seat 138 can allow the receiver member 114 to pivot at various angles relative to the bone anchor. The seat 138 can have a substantially spherical shape that corresponds to the spherically shaped, proximal head 18 of the bone anchor 12 so as to allow the seat 138 to facilitate angular movement of the receiver member 114 relative to the bone anchor 12. A width of the seat 138 can vary between the proximal and distal ends of the receiver member 114, as shown in FIG. 3B, the width being measured as a distance that is perpendicular to the longitudinal axis $L_R$ of the receiver member 114. In general, a distance $D_D$ of the distal opening 136 can be less than a largest distance $D_S$ of the seat. When the distal opening 136 has a circular shape and the seat 138 has a spherical shape, as in the illustrated embodiment, the distance $D_D$ of the distal opening 136 is the diameter of the circle and the distance $D_S$ of the seat is the diameter of the sphere. For example, the distance $D_D$ of the distal opening can be between about 5% to 25% of the largest distance $D_S$ of the seat. The distance $D_D$ of the distal opening 136 relative to the largest distance $D_S$ of the seat 138 can depend in part on the magnitude by which the receiver member 114 can change to accommodate the proximal head 18 of the bone anchor 12, as discussed in detail below. The U-shaped recess 130 of the receiver member 114 can have a distance $D_R$, as shown in FIG. 3B. As used herein, the distance of the distal opening, the distance of the polyaxial seat, and the distance of the U-shaped recess are defined as a horizontal distance that is perpendicular to a longitudinal axis of the receiver member.

One or more features can be formed in the receiver member to allow a size of the seat 138 to be selectively increased and decreased so as to allow the receiver member 114 to be selectively coupled to the bone anchor 12 and to frictionally engage the bone anchor 12, and to be locked with respect the bone anchor 12 in a desired angular position. Referring back to FIG. 3A, in one embodiment a relief slot 140 is formed in the receiver member 114. In the illustrated embodiment, the relief slot 140 is a substantially T-shaped cutout formed in an outer sidewall of a distal portion of the receiver member 114. A relief slot can be sized and shaped in various ways. By way of non-limiting example, the relief slot can be Y-shaped, O-shaped, I-shaped, etc. While not shown, the receiver member includes a second relief slot, which can be the same as or different from the first relief slot, and is formed in an opposite side of the receiver member. When the receiver member 114 is in the configuration of FIG. 3A, a first portion 150 of the relief-slot 140 extends along the longitudinal axis $L_R$ of the receiver member 114 in a proximal-to-distal direction, while a second portion 152 of the relief-slot 140 extends in a direction perpendicular to the first portion 150. In general, a length $L_1$ of the first portion 150 can vary, and it can be in the range of about 10% to 35% of a height $H_1$ of the receiver member 114 from the distal-most surface 134 to a distal-most surface of the recess 130. A length $L_2$ of the second portion 152 can vary, and can be in the range of about 5% to 50% of a largest width $W_1$ of the receiver member 114.

In use, a size of the U-shaped recess of the receiver member can be adjusted in inverse proportionality to a size of the seat to thus allow the receiver member 114 to move between various positions. For example, the receiver member 114 can have a number of different positions including: a resting position in which the receiver member 114 has not been applied to the bone anchor 12 and no force is applied to the receiver member 114; a mating position in which the recess 138 is increased in size to allow the receiver member 114 to be mated to the bone anchor 12; a frictionally engaged position, in which the recess 138 in the receiver member 114 is decreased and engaged with the bone anchor 12 while still allowing polyaxial movement of the bone anchor; and a locked position in which the receiver member 114 is mated to the bone anchor 12 and a size of the recess 138 is further decreased to lock the receiver member 114 in a fixed position relative to the bone anchor 12.

In the embodiment shown in FIGS. 3A and 3B, the arms 128A, 128B of the receiver member 114 are at a neutral location and aligned along the longitudinal axis $L_R$. The opposed sidewalls that define the U-shaped recess 130 thus extend substantially parallel to one another. In one embodiment, the position shown in FIGS. 3A and 3B is a resting position of the receiver member 114, where no other components are mated to the receiver member and no force is applied thereto to change the size of the U-shaped recess 130 and the seat 138. A person skilled in the art will appreciate that while FIGS. 3A and 3B are referred to as a resting position, the resting position can vary and can be the same as or different than any one of the mating position, the frictionally engaged position, the locked position, and any position there between.

Figure 4A:
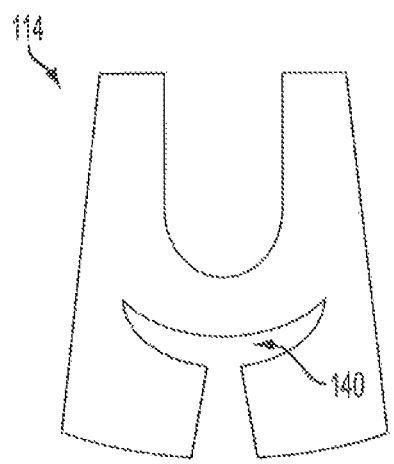
FIG. 4A is a side view of the receiver member of FIG. 2 in another configuration.
Figure 4B:
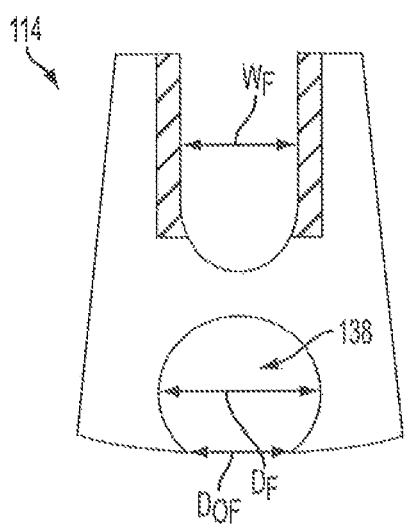
FIG. 4B is a side, cross-sectional view of the receiver member of FIG. 2.

FIGS. 4A and 4B illustrate the receiver member in the mating configuration, in which the arms 128A, 128B of the receiver member 114 are biased toward one another to decrease a size of the U-shaped recess 130 and to increase a size of the seat 138 in the receiver member. In this position, the receiver member 114 is configured to be applied to the bone anchor 12. As shown, a volume of the seat 138 is increased as compared to the volume of the seat in the resting position shown in FIGS. 3A and 3B. In particular, a largest distance $D_F$ of the seat 138 is greater than the largest distance $D_S$ of the seat 138 in the resting configuration. Because the size and shape of the seat 138 defines a size and shape of the distal opening 136, when the receiver member 114 is expanded to the mating configuration, a distance $D_{OF}$ of the distal opening 136 of the receiver member 114 is greater than the distance $D_D$ of the distal opening 136 in the resting position. At the same time, a distance $W_F$ between the arms 128A, 128B of the receiver member 114 is less than a distance $D_R$ between the arms when the receiver member 114 is in the resting position.

Figure 5A:
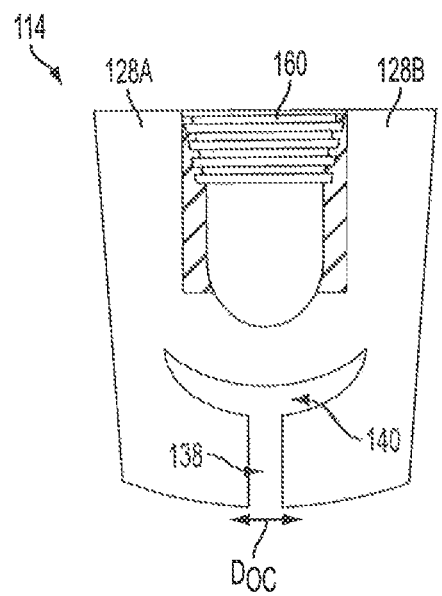
FIG. 5A is a side view of the receiver member of FIG. 2 in a frictionally engaged configuration.
Figure 5B:
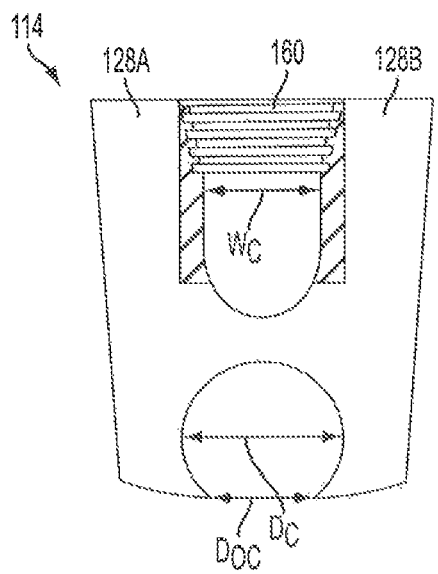
FIG. 5B is a side, cross-sectional view of the receiver member of FIG. 2 in the locked configuration.

FIGS. 5A and 5B show the receiver member 114 in a locked configuration, in which the receiver member 114 is mated to the bone anchor 12 and a closure mechanism 160 is mated to the arms 128A, 128B of the receiver member 114 to lock a spinal fixation element (not shown) therein. The closure mechanism 160 is discussed in more detail below. As shown, a volume of the seat 138 in the locked configuration is smaller than the volume of the seat 138 in the resting position, in part because closure element 160 applies a force that pushes or spreads the arms 128A, 128B outward and away from one another to thereby further compress the seat 138 around a bone anchor. In particular, a largest distance $D_C$ of the seat 138 is less than the largest distance $D_S$ of the seat 138 in the resting configuration. Because the size and shape of the seat 138 defines a size and shape of the distal opening 136, when the receiver member 114 is in the locked configuration, a distance $D_{OC}$ of the distal opening 136 of the receiver member 114 is less than the distance $D_D$ of the distal opening 136 in the resting position. At the same time, a distance $W_C$ between the arms 128A, 128B of the receiver member 114 is greater than a distance $D_R$ between the arms when the receiver member 114 is in the resting position.

While not shown, the frictionally engaged position can be located somewhere between the resting position and the locking position. In the frictionally engaged position, the receiver member 114 is mated to the bone anchor 12 and the seat 138 preferably has a size that is configured to engage the head 18 of the bone anchor 12 to retain the bone anchor 12 within the seat 138 and thereby mate the bone anchor 12 to the receiver member 114, while still allowing the bone anchor 12 to move polyaxially relative to the receiver member 114.

A person skilled in the art will appreciate that the geometry and sizes of the U-shaped recess 130 and the seat 138 in the receiver member 114 can vary. In one exemplary embodiment, the distance between the arms in the resting position can be in the range of about 5 mm to 7 mm, in the mating engaged position can be in the range of about 3 mm to 6 mm, in the frictionally engaged position can be in the range of about 5.2 mm to 7.2 mm, and in the locked position can be in the range of about 5.5 mm to 10 mm. In one exemplary embodiment, the largest distance of the seat in the resting position can be in the range of about 6 mm to 10 mm, in the mating engaged position can be in the range of about 6.5 mm to 12 mm, in the frictionally engaged position can be in the range of about 5.8 mm to 9.8 mm, and in the locked position can be in the range of about 5.5 mm to 9.5 mm. In one exemplary embodiment, the distance of the distal opening in the resting position can be in the range of about 5 mm to 9 mm, in the mating engaged position can be in the range of about 5 mm to 10 mm, in the frictionally engaged position can be in the range of about 4.8 mm to 9.8 mm, and in the locked position can be in the range of about 4.5 mm to 9.5 mm. In another embodiment, by way of non-limiting example, the distance of the distal opening can change by about ±25%, the distance of the seat can change by about ±35%, and the distance between the arms can change by about ±75% as the receiver member is moved between the various positions.

The relief slot 140 can facilitate movement between the various positions, and the shape of the relief slot 140 can vary as the receiver member 114 is moved between the various positions. For example, in the mating configuration, shown in FIG. 4B, the relief slot 140 can curve upward in a proximal direction, that is, a proximal-most edge of the second portion 152 of the slot 140 can be concave. When the receiver member 114 is in the frictionally engaged (not shown) or locked position, shown in FIG. 5A, the second portion 152 of the T-shaped relief slot 140 can have a more pronounced concave-up shape.

The receiver member 114 can move between the above-described configurations in various ways. In one embodiment, the receiver member 114 can be moved from the resting position, shown in FIGS. 3A and 3B, to the mating configuration, shown in FIGS. 4A and 4B, by applying an inwardly directed, compressive force to the arms 128A, 128B. While applying the inwardly directed force, the receiver member 114 can be placed onto the head of a bone anchor 12, as the distal opening 136 and the seat 138 can be increased to a size sufficient to receive the head of the bone anchor 12 therein. Once so placed, the force can be released thereby allowing the receiver member 114 to return toward the resting position and in particular to move to the frictionally engaged position. In an exemplary embodiment, the resting position is the same as the frictionally engaged position. Once the head of the bone anchor 12 is seated within the receiver member 114, and it is desired to lock the receiver member in a fixed position relative to the bone anchor, an outwardly directed, expanding force can be applied to the arms of the receiver member 114, e.g., by applying a closure mechanism 160 to compress the seat around the anchor.

Figure 6A:
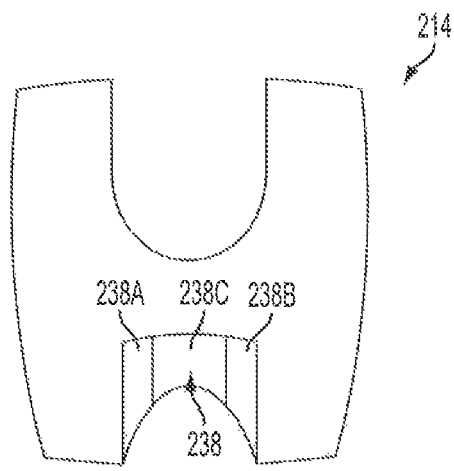
FIG. 6A is a cross-sectional view of another embodiment of a receiver member.
Figure 6B:
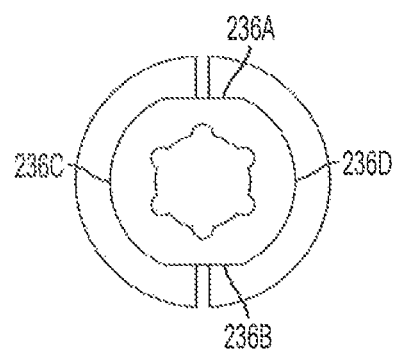
FIG. 6B is a bottom view of the receiver member of FIG. 6A.
Figure 6C:
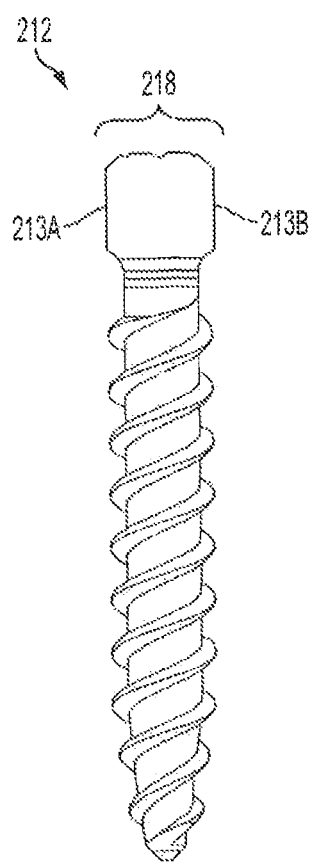
FIG. 6C is a side view of a bone anchor for use with the receiver member of FIG. 6A.

FIGS. 6A and 6B illustrate another embodiment of a receiver member 214. As shown, the receiver member 214 includes a seat 238 having first and second planar sidewalls 238A, 238B and third and fourth spherically-shaped sidewalls 238C, 238D for receiving at least a portion of the bone anchor therein. Because FIG. 6A is a cross-sectional, side view of the receiver member 214, the fourth side 238D is not shown. The sidewalls extend in a proximal-distal direction and together define the seat for seating a head of a bone anchor. The first and second planar sides 238A, 238B can extend parallel to a longitudinal axis $L_R$ of the receiver member 214. This receiver member 214 can be configured to seat a bone anchor 212 having first and second planar sides 213A, 213B, as shown in FIG. 6C. When the bone anchor 212 is positioned in the seat 238, the first and second planar sides 238A, 238B can compress around the head 218, directly contacting the head 218 and preventing it from angularly pivoting along an axis that is perpendicular to the first and second planar sides 238A, 238B. As a result, the bone anchor 212 can be limited to pivotal movement along a single plane that is parallel to the first and second planar sides 238A, 238B of the receiver member 214 and first and second planar sides 213A, 213B of the bone anchor 218. As in the previous embodiment, the seat 238 also defines a four-sided distal opening 236, as shown. More specifically, the distal opening 236 includes first and second opposed edges 236A, 236B which are straight and parallel to each other, and third and fourth opposed edges 236C, 236D which are curved or arc-shaped. These edges 236A, 236B, 236C, and 236C are defined by the size, shape, and configuration of the four sides 238A, 238B, 238C, and 238D of the seat 238 discussed above. As shown in FIG. 6B, the first and second opposed edges 236A, 236B can have an identical length and the third and fourth opposed edges 236C, 236D can have an identical radius of curvature such that the distal opening 236 has a substantially symmetrical shape.

Figure 7A:
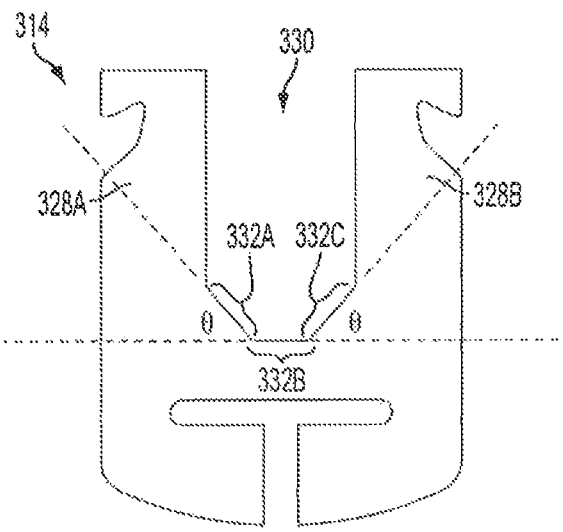
FIG. 7A is a side view of yet another embodiment of a receiver member.
Figure 7B:
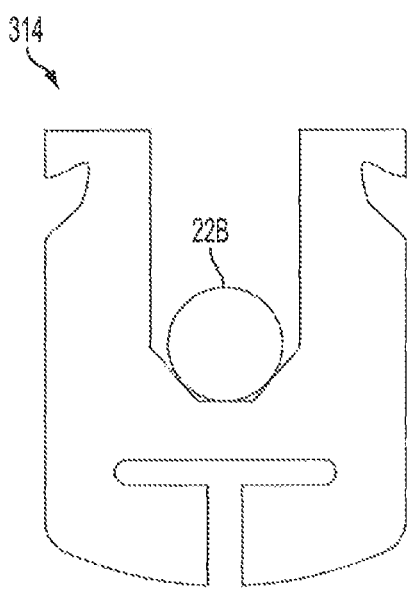
FIG. 7B is a side view of the receiver member of FIG. 7A having a smaller sized spinal fixation element positioned therein.
Figure 7C:
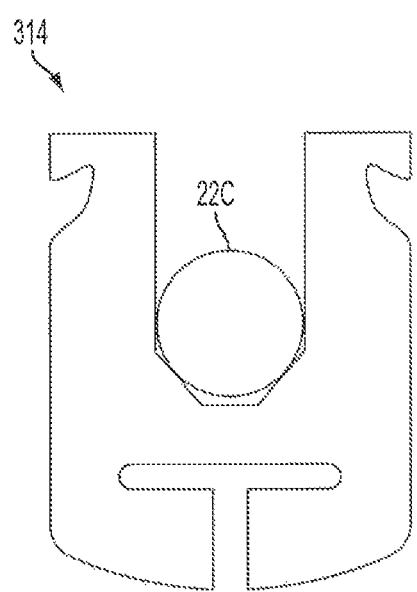
FIG. 7C is a side view of the receiver member of FIG. 7A having a larger sized spinal fixation element positioned therein.

A receiver member can include features that facilitate receipt of various sized and shaped fixation elements. For example, FIGS. 7A-7C illustrate a receiver member 314 having a modified U-shaped recess 330 configured to receive various sized and shaped spinal fixation elements. The receiver can have any combination of features described herein. As shown in FIG. 7A, walls of the U-shaped recess 330 includes a first planar surface 332A, second planar surface 332B, and third planar surface 332C. While not shown, the U-shaped recess 330 has corresponding fourth, fifth, and sixth planar surfaces on an opposite side of the receiver member 314. The first, second, and third planar surfaces 332A, 332B, 332C can also extend at an angle θ relative to an axis perpendicular to the longitudinal axis $L_R$ of the receiver member 314. By way of non-limiting example, the first and third planar surfaces 332A, 332C can extend at an angle θ in the range of about 30 to 60 degrees, while the second planar surface 332B can extend substantially perpendicular to the longitudinal axis $L_R$ of the receiver member. Respective lengths of each of the first, second, and third planar surfaces 332A, 332B, 332C and the magnitude of angle θ can dictate a size of a spinal fixation element that can be received in the modified U-shaped recess 330. For example, FIG. 7B shows a spinal rod 22B positioned in the modified U-shaped recess 330 and FIG. 7C shows a second spinal rod 22C positioned in the recess 330, the first spinal rod 22B having a smaller diameter than a diameter of the second spinal rod 22C.

Figure 8A:
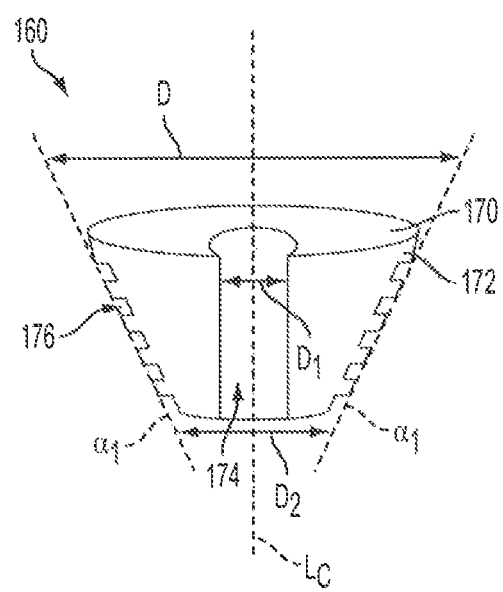
FIG. 8A is a cross-sectional, side view of a closure mechanism, according to one embodiment.

A closure mechanism is also provided for securing or locking a spinal fixation element within a receiver member and angularly fixing a bone anchor relative to a receiver member. The closure mechanism can have various sizes, shapes, and configurations. FIG. 8A illustrates a cross-sectional, side view of one embodiment of a closure mechanism 160 that is in the form of a single set screw 170. As shown, the set screw 170 can have a thread 172 formed on an outer surface thereof for threadably engaging the inner thread on each arm of a receiver member. The set screw 170 can have a bore 174 formed therein configured to mate with and to permit engagement to a driving tool (not shown), such as by a press-fit. In the illustrated embodiment, the bore 174 has a cylindrical shape with a central longitudinal axis $L_1$ extending through a center of the bore 174. The bore 174 can be shaped in other ways, such as rectangular, hexagonal, octagonal, etc., and the shape of the bore 174 can correspond to the shape of the distal end of the driving tool. An inner diameter $D_1$ of the bore 174 can be substantially constant or the inner diameter $D_1$ of the bore 174 can vary in the proximal-to-distal direction along the central longitudinal axis $L_C$. In the illustrated embodiment, outer surface of the closure mechanism 160 is tapered in a proximal-to-distal direction along the central longitudinal axis $L_1$, that is, a proximal diameter $D_1$ of the set screw 170 can be larger than a distal diameter $D_2$ of the set screw 170. The taper of the outer surface of the closure mechanism 170 can be characterized by an angle $\alpha_1$, shown in FIG. 8A, the angle $\alpha_1$ being measured between an axis defined by the distal diameter $D_2$ of the set screw 170 and an outer surface of the set screw 170. As shown, the angle $\alpha_1$ can be in the range of about 1 to 20 degrees. A larger angle $\alpha_1$ can indicate a steeper, more pronounced taper and a smaller angle $\alpha_1$ can indicate a gradual, less pronounced taper. The taper of the set screw 170 can also be characterized by the ratio of the proximal diameter $D_1$ of the set screw 170 to the distal diameter $D_2$ of the set screw 170, which can be in the range of about 1 to 20 degrees. As will be discussed below, when the set screw 170 is threaded into a receiver member, the tapered outer surface can exert an outwardly directed force on the arms of the receiver member to close the distal opening and decrease the size of the seat of the receiver member. The set screw can thus lock a spinal fixation element in the receiver member and angularly fix the receiver member relative to the bone anchor, providing dual-locking, as shown in FIG. 8A. The closure mechanism can vary in other ways. In one embodiment, the closure mechanism can have a stepped diameter rather than a gradual taper. In another embodiment, the diameter of the closure mechanism can be constant and sized to fit between arms of the receiver member when the receiver member is expanded to the configuration of FIGS. 5A and 5B. When the diameter of the closure mechanism is constant and is sized to fit between the arms of an expanded receiver member, one or more features or instruments can be used to help direct the closure mechanism into the receiver member. For example, an inner surface of each of the arms can have a distal slope from a proximal-most end toward the distal end, and this can help guide the closure mechanism between the arms of the receiver member. In yet another embodiment, the closure mechanism can be configured to twist lock or snap-fit in the receiver member. A person skilled in the art will also appreciate that, while a single closure mechanism is shown, the closure mechanism can include multiple components, such as inner and outer components. Various closure mechanisms known in the art can be used. Additionally, the size and degree of taper of the closure mechanisms can be varied to achieve the desired results.

Figure 8B:
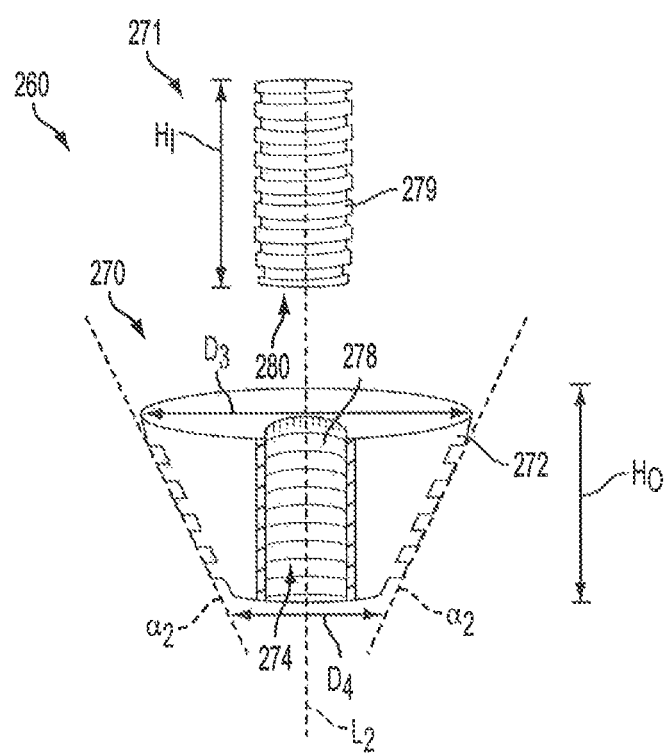
FIG. 8B is an exploded, cross-sectional view of a closure mechanism that includes inner and outer closure elements, according to another embodiment.

FIG. 8B illustrates an embodiment of a two-piece closure mechanism 260 having an inner set screw 271 for locking a spinal fixation element in the receiver member and an outer set screw 270 for fixing an angle of the receiver member relative to the bone anchor. As shown, the outer set screw 270 can have a thread 272 formed on an outer surface thereof configured to threadably engage an inner thread provided on the arms of the receiver member. Similar to the previous embodiment, the outer set screw 270 can be tapered in a proximal-to-distal direction along longitudinal axis $L_2$, that is, a proximal diameter $D_3$ of the outer set screw 270 can be larger than a distal diameter $D_4$ of the outer set screw 270. The taper of the outer surface of the outer set screw 270 can be characterized by an angle $\alpha_2$ being measured between an axis defined by the distal diameter $D_4$ of the set screw 270 and an outer surface of the set screw 270. When the outer set screw 270 is screwed into a receiver member, the tapered outer surface of the outer set screw 270 can exert an outwardly directed force on arms of a receiver member to close the distal opening of the receiver member. The outer set screw 270 can further include a bore 274 having a thread 278 formed on an inner surface thereof for threadably engaging an outer thread 279 of an inner set screw 271. As shown in FIG. 8B, the bore 274 of the outer set screw 270 has a substantially cylindrical shape that corresponds to the shape of the inner set screw 271. In this embodiment, the inner set screw 271 has a height $H_1$ that is greater than a height $H_O$ of the outer set screw 270. In this way, when the inner set screw 271 is positioned in the bore 274, a distal surface 280 of the inner set screw 271 can directly contact a fixation rod positioned in a receiver member to lock the rod therein. In other embodiments, the height $H_1$ of the inner set screw 271 can be less than or equal to the height $H_O$ of the outer set screw 270. In an exemplary embodiment, where a two-piece closure mechanism is utilized, the receiver member can also include a compression cap disposed therein for allowing separate locking of the spinal fixation element relative to the receiver member and of the receiver member relative to the bone anchor.

Figure 9A:
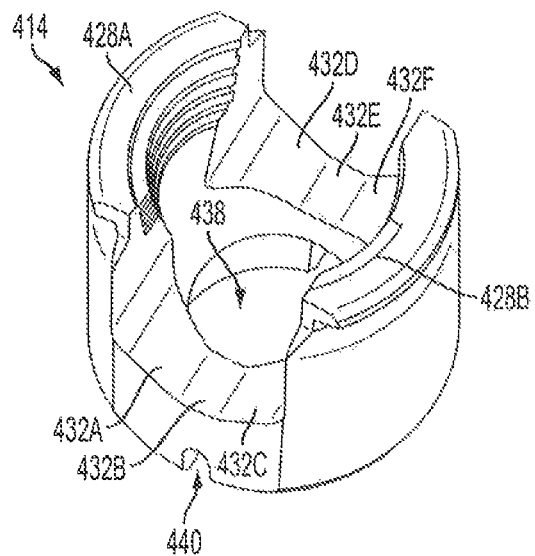
FIG. 9A is a perspective view of another embodiment of a receiver member having a combination of features.
Figure 9B:
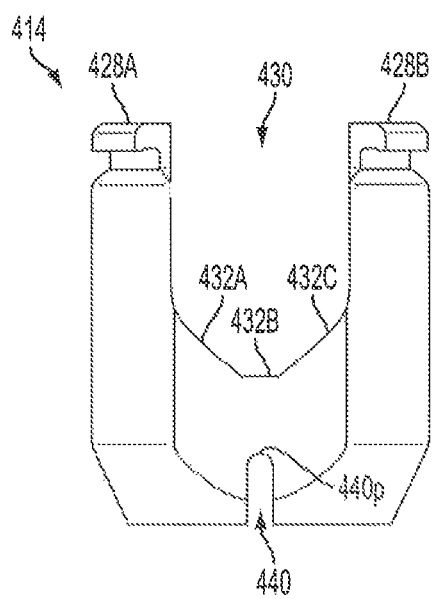
FIG. 9B is a side view of the receiver member of FIG. 9A.
Figure 9C:
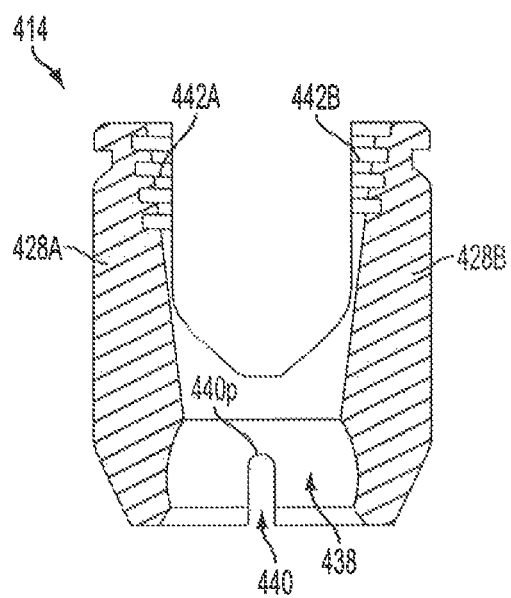
FIG. 9C is a cross-sectional, side view of the receiver member of FIG. 9A.

As previously mentioned, the receiver members, bone anchors, closure mechanisms, and spinal fixation elements can have any combination of features previously described. For example, FIGS. 9A-9C illustrate another embodiment of a receiver member 414. The receiver member 414 has first and second arms 428A, 428B with threads 442A, 442B formed thereon for threadably engaging and mating with any closure mechanism described herein or known in the art. In this embodiment, the receiver member 414 has two relief slots (one relief slot 440 is shown). Rather than having a Y-shape, the relief slots 440 extend in a distal-to-proximal direction on the receiver member 414 and terminate in a curved proximal-most end 440*p*. In this embodiment, the distal opening 436 of the receiver member 414 has a substantially circular shape and the polyaxial seat 438 has a substantially spherical shape. Further, a U-shaped recess 430 extending between the first and second arms 428A, 428B has three planar surfaces 432A, 432B, 432C on a first side of the receiver member 414, and three planar surfaces 432D, 432E, 432F on a second, opposite side of the receiver member 414 that can help seat various sized spinal fixation elements therein.

The various bone anchor assemblies disclosed herein can be implanted in bone using various techniques. For example, FIGS. 10A, 10B, 11, 12A, and 12B illustrate a bone anchor 12 implanted in a vertebra. While the bone anchor assembly is shown with receiver member 114, bone anchor 12, and closure mechanism 270, a person skilled in the art will appreciate that any combination of the receiver members and closure mechanisms disclosed herein can be used.

In use, a vertebra 13 can be prepared to receive a bone anchor assembly 200, generally by drilling a hole in the bone which is sized appropriately to receive the bone anchor 12. The bone anchor 12 can be driven into the prepared hole via a driver tool fitted into the bore or recess (not shown) in the proximal head 18 of the bone anchor 12. In a preferred embodiment, the bone anchor 12 is attached to the receiver member 114 via bottom-loading, in which the proximal head 18 of the bone anchor 12 is leading as it is inserted into the seat 138 of the receiver member 114. The bone anchor 12 can be bottom-loaded into the receiver member 114 after the anchor 12 is inserted into bone. In another, less preferred embodiment, the receiver member can be attached to the bone anchor before the bone anchor is driven into the bone.

Figure 10A:
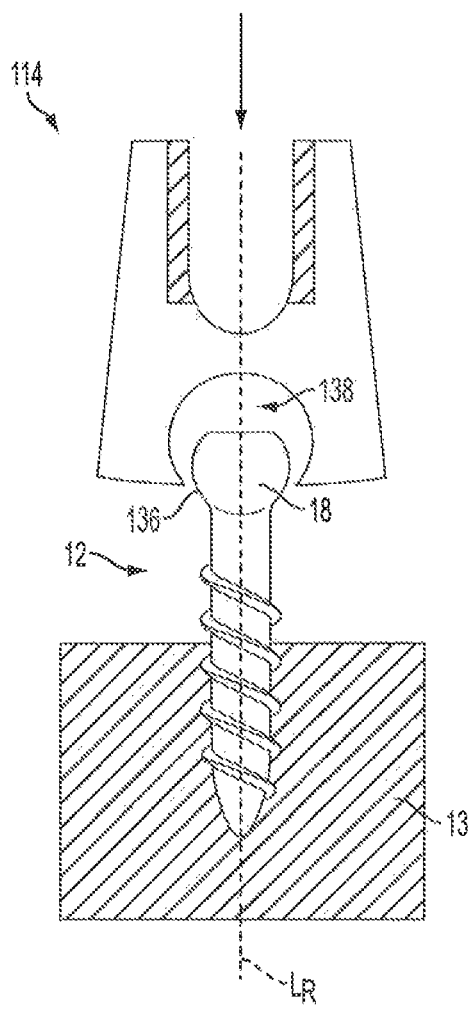
FIG. 10A is a cross-sectional view of the receiver member of FIG. 2 and a bone anchor being inserted in a vertebra using a first method.
Figure 10B:
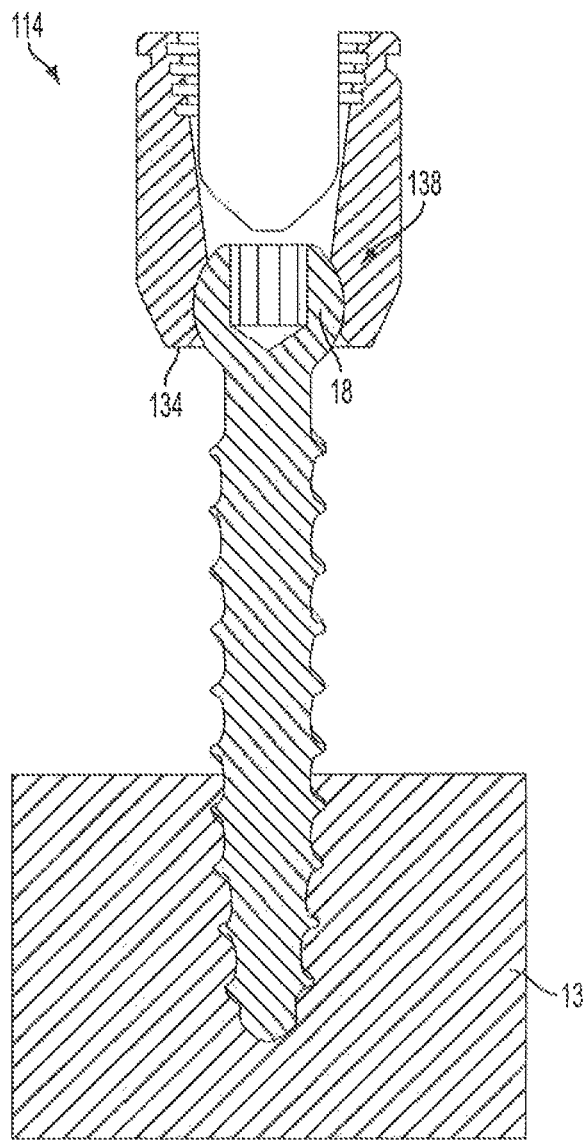
FIG. 10B is a cross-sectional view of the receiver member of FIG. 2 showing the bone anchor seated or frictionally engaged in the receiver member.

The receiver member 114 can be mated with the bone anchor 12 using various techniques which can depend in part on a diameter of the proximal head 18 of the bone anchor 12 relative to a size of the seat 138 formed in the receiver member 114. For example, when the head 18 of the bone anchor 12 is larger than a size $D_S$ of the distal opening 136 of the receiver member 114, the head 18 can be forced into the distal 136 opening by means of a press-fit. More specifically, one or more external forces can be applied along a longitudinal axis $L_R$ of the receiver member 114 and the bone anchor 12 until the proximal head 18 of the bone anchor 12 increases a size of the distal opening 136. In this way, the proximal head 18 of the anchor 12 can be received in the seat 138 of the receiver member 114. The direction of the applied external force is illustrated in FIG. 10A using an arrow. FIG. 10A also shows the proximal head 18 of the bone anchor 12 resting against the distal opening 136 of the receiver member 114 prior to be seated therein. A size and location of the relief slot(s) (not shown) formed in the receiver member 114 can influence the magnitude of force required to assemble or mate the receiver member 114 with the bone anchor 12, as previously described. When the head 18 of the bone anchor 12 is positioned in the seat 138 of the receiver member 114, as shown in FIG. 10B, the external force can be released. This can cause a size of the seat 138 and a size of the distal opening 136 to automatically decrease and compress around the bone anchor 12. If the seat 138 is polyaxial, as in the illustrated embodiment, after the seat 138 has collapsed around the proximal head 18 of the anchor 12 the receiver member 114 can be angularly oriented relative to the bone anchor 12. If the seat is uni-planar seat, as in seat 238 of the receiver member 214 shown in FIGS. 6A-6B, the receiver member can pivot uniplanarly in a single plane relative to the bone anchor, as previously discussed. The seat 238 and the distal opening 236 can thus compress around and frictionally engage the head 218 of the bone anchor 212 to prevent the bone anchor from detaching from the receiver member 214, yet will permit a desired angulation of the components relative to one another and resist applied correctional forces.

Figure 11:
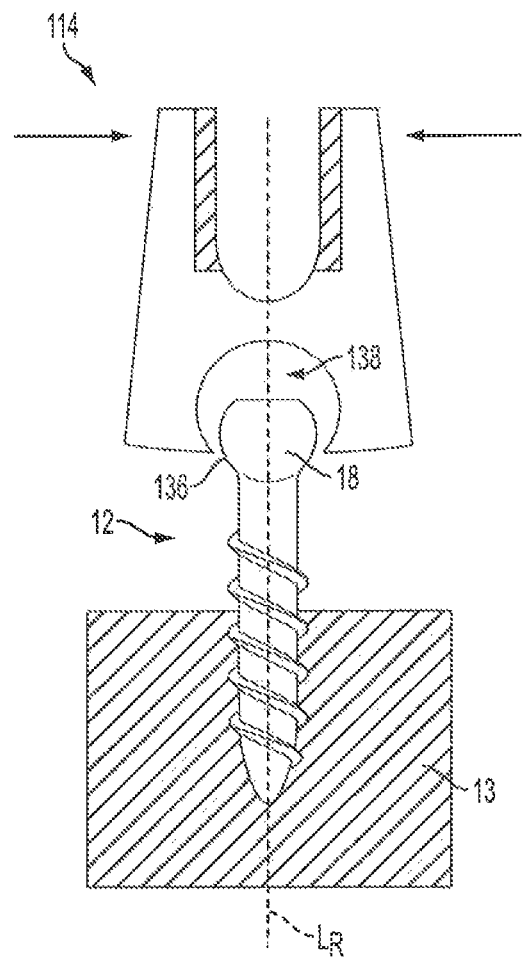
FIG. 11 is a side view of the receiver member of FIG. 2 and a bone anchor being inserted in a vertebra using a second method.

Alternatively, the receiver member can be mated to the bone anchor by applying a force to the proximal end of the receiver member. As shown in FIG. 11, an inwardly directed clamping force, shown using arrows, can be applied to both of the arms 128A, 128B of the receiver member 114 to decrease a distance between the arms 128A, 128B. This external force can be applied to the receive member 114 manually and/or using a clamping tool. As in the previous embodiment, the external force can cause a size of the seat 138 and a size of the distal opening 136 to increase, in part because of the relief-slot(s) (not shown) formed in the receiver member 114. When the receiver member 114 is in this configuration, the distance of the distal opening 136 can be large enough to allow the proximal 18 head of the bone anchor 12 to pass therethrough and the distance of the seat 138 can be large enough to accommodate the proximal head 18 of the bone anchor 12. When the proximal head 18 of the bone anchor 12 is positioned in the seat 138, the external force can be released. This can cause the seat 138 of the receiver member 114 to compress around the proximal head 18 of the anchor 12. As in the previous embodiment, the seat 138 and the distal opening 136 can thus compress around the head 18 of the bone anchor 12 to prevent the bone anchor 12 from detaching from the receiver member 114, yet can permit a desired angulation of the components relative to one another (i.e. polyaxial or uniplanar).

Figure 12A:
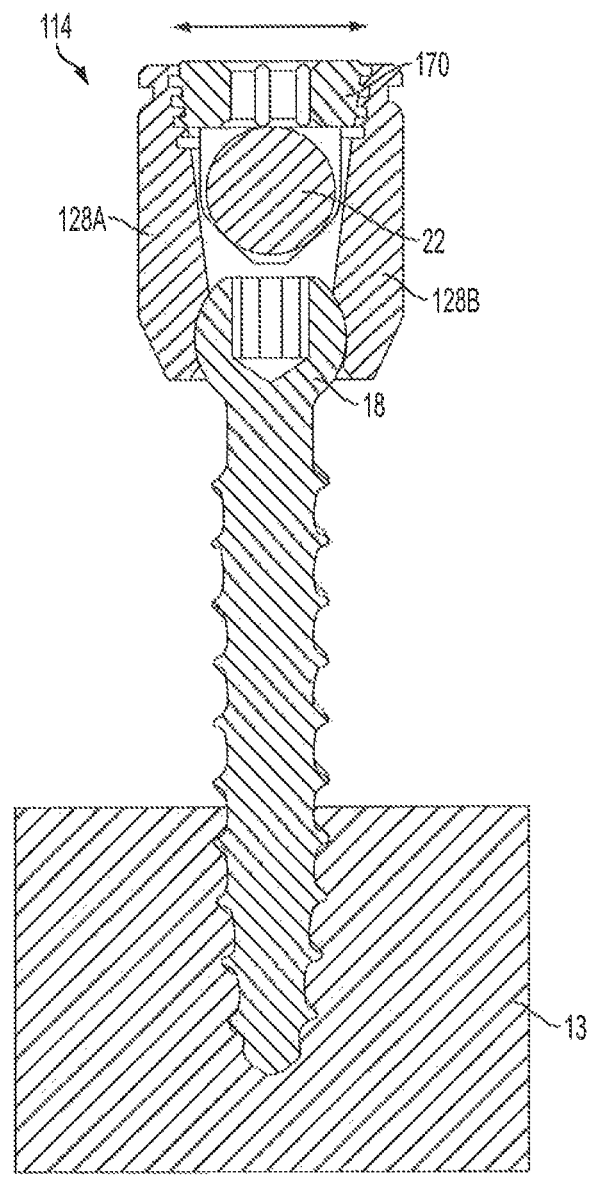
FIG. 12A is a side, cross-sectional view of the receiver member of FIG. 2 showing a first closure mechanism locking a spinal fixation element in the receiver member.
Figure 12B:
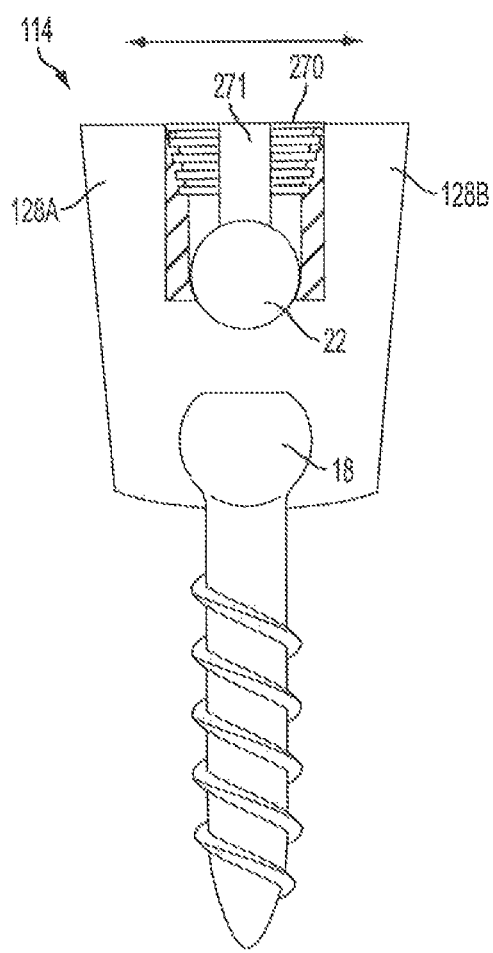
FIG. 12B is a side, cross-sectional view of the receiver member of FIG. 2 having a second closure mechanism locking a spinal fixation element in the receiver member.

Once the bone anchor 12 is positioned in the bone and the receiver member 114 is attached thereto, the receiver member 114 can be pivoted or angulated relative to the bone anchor 12 via the seat 138, which can be polyaxial or uniplanar. One or more bone anchor assemblies (not shown) can also be deployed into bone using the same or different techniques. A spinal fixation element, e.g. spinal rod 22, can be positioned in the recess U-shaped recess 130 of the receiver member 114 and can be manipulated in various ways using various tools so that the spinal rod 22 extends through one or more bone anchor assemblies. Manipulating the spinal rod 22 can change an angle of the receiver member 114 relative to the bone anchor 12. When the spinal rod 22 is in a desired position, a closure mechanism 160 can be engaged with the inner thread provided on the arms 128A, 128B, of the receiver member 14. When the closure mechanism 160 is a single set screw 170, a torsional force or rotational force can be applied to the closure mechanism 160 to move it distally toward the spinal rod 22. As the closure mechanism 160 is moved distally, the taper on the outer surface can increase the distance between the arms 128A, 128B of the receiver member 114. Successive rotations of the closure mechanism 160 relative to the receiver member 114 can apply an outwardly directed force, shown in FIGS. 12A and 12B using an arrow, on the arms 128A, 128 to cause the seat 138 to compress around the head 18 of the bone anchor 12, thereby angularly fixing the receiver member 114 relative to the bone anchor 12. In one embodiment, the torsional force can be applied to the single set screw 170 until a distal surface of the set screw 170 directly contacts the spinal rod 22, as shown in FIG. 12A. In this embodiment, the single set screw 170 can angularly fix the bone anchor 12 relative to the receiver member 114 and lock the rod 22 within the receiver member. Alternatively, when a closure mechanism 260 consists of an inner set screw 271 and a tapered outer set screw 270, as in FIG. 12B, torsional forces can be applied to the tapered outer set screw 270 to move it distally toward the spinal rod 22. However, in this embodiment, a distal surface of the outer set screw 270 need not directly contact the rod 22. Rather, the inner set screw 271 can be inserted in the bore 274 of the outer set screw 272 and can be engaged with the thread 278 on the inner surface of the outer set screw 270. Torsional forces can then be applied to the inner set screw 271 to move it distally relative to the outer set screw 270 toward the spinal rod, until the inner set screw 271 directly contacts the spinal rod 22. When the inner set screw 271 directly contacts the spinal rod 22, this can fix the spinal rod 22 relative to the receiver member 114 and the bone anchor 12.

Bone anchor assemblies of the type describe above can be used to treat a variety of conditions, such as scoliosis. A person skilled in the art will appreciate that the present invention has application in conventional minimally-invasive and open surgical instrumentation as well application in robotic-assisted surgery.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A bone anchor assembly, comprising:
   a bone anchor having a proximal head and a distal threaded portion; and
   a receiver member having a proximal portion with opposed arms configured to receive a spinal fixation rod therebetween, the opposed arms of the receiver member defining a U-shaped recess having opposed planar surfaces for seating spinal fixation rods of differing diameters, the opposed planar surfaces extending at an oblique angle relative to a longitudinal axis of the receiver member, the receiver member having a distal portion having a polyaxial seat formed therein and configured to polyaxially seat the proximal head of the bone anchor, and the opposed arms having interior receiver threads, the receiver threads having a major diameter that increases in a distal-to-proximal direction when the opposed arms are parallel to each other, the receiver member having opposed relief slots formed therein, each slot having a first portion that extends parallel to the longitudinal axis of the receiver member and a second portion that is substantially perpendicular to the first portion;
   wherein the opposed arms are configured to move toward one another to cause a size of the polyaxial seat to increase and to cause the second portions of the slots to form a crescent shape, and the opposed arms are configured to move away from one another to cause the size of the polyaxial seat to decrease.

2. The bone anchor assembly of claim 1, wherein the relief slots are configured to allow the opposed arms to move toward and away from one another and to allow the size of the polyaxial seat to increase and decrease.

3. The bone anchor assembly of claim 1, wherein the opposed relief slots extend proximally from a distal-most end of the receiver member.

4. The bone anchor assembly of claim 2, wherein the relief slots are substantially T-shaped.

5. The bone anchor assembly of claim 1, further comprising a closure mechanism configured to mate to the interior receiver threads of the opposed arms and to cause the opposed arms to move away from one another such that the distal portion of the receiver member compress around the proximal head of the bone anchor to prevent removal of the proximal head from the polyaxial seat in the receiver member.

6. The bone anchor assembly of claim 5, wherein the closure mechanism comprises a threaded set screw having an outer diameter that increases in a distal-to-proximal direction.

7. The bone anchor assembly of claim 1, wherein an outer diameter of the proximal head of the bone anchor is greater than a size of an opening formed in a distal end of the receiver member and extending into the polyaxial seat.

8. The bone anchor assembly of claim 1, wherein the polyaxial seat is configured to frictionally engage the proximal head of the bone anchor when the head is seated therein and no closure mechanism is applied to the receiver member.

9. The bone anchor assembly of claim 1, wherein the receiver member includes opposed flat surfaces formed therein and configured to limit movement of the distal threaded portion of the bone anchor along a single plane of motion.

10. A method for implanting a bone anchor, comprising:
    implanting a threaded shank of a bone anchor in bone;
    coupling a proximal head of the threaded shank to a receiver member having at least one relief slot formed therein, the slot having a first portion that extends parallel to a longitudinal axis of the receiver member and a second portion that is substantially perpendicular to the first portion, the second portion forming a crescent shape as the head is coupled to the receiver member;
    positioning a spinal fixation rod within a u-shaped recess in the receiver member, the u-shaped recess having a plurality of planar surfaces for seating spinal fixation rods of differing diameters;
    applying a closure mechanism that includes an inner set screw and an outer set screw to the receiver member;
    tightening the outer set screw to cause a distal portion of the receiver member to compress around the proximal head of the bone anchor and thereby lock the receiver member in a fixed position relative to the bone anchor; and tightening the inner set screw such that it directly contacts the spinal fixation rod to lock the rod in the u-shaped recess.

11. The method of claim 10, wherein the outer set screw is threaded into a proximal portion of the receiver member.

12. The method of claim 10, wherein the closure mechanism is tapered such that the closure mechanism causes opposed proximal arms of the receiver member to move away from one another thereby causing the distal portion of the receiver member to compress around the proximal head of the bone anchor.

13. The method of claim 10, wherein the receiver member is limited to movement within a single plane of motion relative to the bone anchor.

14. A bone anchor system, comprising:
   a bone anchor having a proximal head and a distal threaded portion;
   a cylindrical spinal fixation rod;
   a monolithic receiver member having:
      a proximal portion with opposed arms configured to receive the spinal fixation rod therebetween,
      the opposed arms of the receiver member defining a U-shaped recess having first and second opposed planar surfaces for seating spinal fixation rods of differing diameters,
      the opposed planar surfaces extending at an oblique angle relative to a longitudinal axis of the receiver member and extending from a flat distal surface that is perpendicular to the longitudinal axis of the receiver member,
      the opposed arms having interior receiver threads, the receiver threads having a diameter that increases in a distal-to-proximal direction,
      opposed T-shaped relief slots formed in the receiver member having a first portion that extends along the longitudinal axis of the receiver member and a second portion that is substantially perpendicular to the first portion, and
      the receiver member having a distal portion having a polyaxial seat formed therein and configured to polyaxially seat the proximal head of the bone anchor;
   a closure mechanism that includes:
      an outer set screw that is tapered such that the outer set screw is configured to cause the opposed arms of the receiver member to move away from one another thereby causing the polyaxial seat of the receiver member to compress around the proximal head of the bone anchor, and
      an inner cylindrical set screw that is configured to secure the spinal fixation rod in the monolithic receiver member,
   wherein the opposed arms are configured to move toward one another to cause a size of the polyaxial seat to increase, and to cause the second portion of the T-shaped slots to form a crescent shape.

* * * * *